US008318104B2

(12) United States Patent
Lewis et al.

(10) Patent No.: US 8,318,104 B2
(45) Date of Patent: Nov. 27, 2012

(54) WASTE TREATMENT APPARATUS AND METHOD

(76) Inventors: Robert W. Lewis, Charlotte, NC (US); Timothy Barrett, Douglassville, PA (US)

( * ) Notice: Subject to any disclaimer, the term of this patent is extended or adjusted under 35 U.S.C. 154(b) by 0 days.

(21) Appl. No.: 13/065,154

(22) Filed: Mar. 15, 2011

(65) Prior Publication Data

US 2011/0165035 A1 Jul. 7, 2011

Related U.S. Application Data

(62) Division of application No. 11/431,260, filed on May 10, 2006, now Pat. No. 7,931,860.

(51) Int. Cl.
*A61L 2/00* (2006.01)
*B09B 3/00* (2006.01)
*B08B 1/02* (2006.01)
*B08B 3/00* (2006.01)

(52) U.S. Cl. ........ 422/298; 422/295; 422/297; 422/299; 422/300; 422/305; 422/308; 422/309; 588/312; 588/321; 588/900; 134/30; 134/31; 134/32; 134/48; 261/DIG. 10; 261/DIG. 65; 261/DIG. 76

(58) Field of Classification Search ............ 422/26, 422/28, 32, 105, 119, 295, 297–300, 305, 422/308–309; 588/312, 321, 900; 134/30–32, 134/48; 261/DIG. 10, DIG. 65, DIG. 76
See application file for complete search history.

(56) References Cited

U.S. PATENT DOCUMENTS 5,270,000 A * 12/1993 Goldner et al. ............... 422/21

* cited by examiner

*Primary Examiner* — Jill Warden
*Assistant Examiner* — Monzer Chorbaji
(74) *Attorney, Agent, or Firm* — John F. A. Earley, III; Frank J. Bonini, Jr.; Harding, Earley, Follmer & Frailey, P.C.

(57) ABSTRACT

An apparatus for treating waste comprises a gravity drop steam heating tower for heating the waste to the biological kill temperature using pressurized steam, a first feed member for feeding the waste to be sterilized to the gravity drop steam heating tower, and a vaporization system. The vaporization system includes a heating chamber for facilitating vaporization of liquids in the waste, a conveying member for conveying the waste from the lower end portion of the gravity drop steam heating tower into and through the heating chamber, and a vaporization chamber for receiving the waste from the heating chamber and for releasing vapor entrained in the waste into the vaporization chamber.

35 Claims, 6 Drawing Sheets

WASTE TREATMENT APPARATUS AND METHOD

CROSS REFERENCE TO RELATED APPLICATIONS

This divisional application is based on and claims priority and benefit under 35 U.S.C. §120 of U.S. patent application Ser. No. 11/431,260, which was filed on May 10, 2006 now U.S Pat. No. 7,931,860 and which is incorporated herein by reference.

BACKGROUND OF THE INVENTION

1. Field of the Invention

This invention relates to a steam sterilization system for sterilization of items such as regulated medical waste, and more particularly concerns a steam sterilization system for sterilization of items such as regulated medical waste on a commercial scale.

2. Description of the Prior Art

Presently, medical waste processing apparatuses designed for commercial use often are ineffective with respect to the vaporization of liquids in the waste stream. Further, some such medical waste processing apparatuses have proven less than effective in destroying pathogenic organisms.

SUMMARY OF THE INVENTION

It is an object of the invention to provide a waste treatment apparatus that facilitates vaporization of liquids in the waste stream.

Another object of the invention is to provide a waste treatment apparatus that facilitates destruction of pathogenic organisms found in the waste stream.

These and other objects are provided by our invention which is set out below.

In a preferred embodiment of our invention, the waste treatment apparatus comprises a gravity drop steam heating tower for heating the waste to the biological kill temperature using pressurized steam, a first feed member for feeding the waste to be sterilized to the gravity drop steam heating tower, a first vaporization system into which the waste treated in the gravity drop steam heating tower is fed, followed by a second vaporization system into which the waste material treated in the first vaporization system is fed.

Each vaporization system includes a heating chamber for facilitating vaporization of liquids in the waste, and a vaporization chamber for receiving the waste from the heating chamber and for releasing vapor entrained in the waste into the vaporization chamber.

Preferably, a hopper is provided for holding the waste material that is to be treated and from which the first feed member draws waste to be fed to the gravity drop steam heating tower. In this preferred embodiment of the invention, a shredder is provided to shred the waste material to the desired particle size, the shredder being integral with the hopper.

Also, in a preferred embodiment of the invention, the waste treatment apparatus is provided with a material handling system to feed waste material to be treated to the hopper, and a de-misting and a high efficiency particulate airborne (HEPA) filter system for condensing mist entrained in the air of the material handling system, the shredder, and the hopper and for collecting airborne pathogens contained in such air. Also, in a preferred embodiment of the invention, the waste treatment apparatus includes a hot water spray down system for spraying waste water onto the interior wall of the gravity drop steam heating tower to clean it, and a controller for controlling the operation of the waste treatment apparatus.

Further, in a preferred embodiment of the invention, an adjustable surge pressure monitor is provided at each surge area to signal when a surge area is approaching becoming overfull.

DETAILED DESCRIPTION

Turning now to the drawings, there is shown a waste treatment apparatus 11 for sterilization of waste material, such as regulated medical waste. The waste treatment apparatus 11 has a gravity drop steam heating tower 13 for heating the waste material to be treated by the waste treatment apparatus 11 to the biological kill temperature using pressurized steam. The gravity drop steam heating tower 13 has an upper end portion 15 having an entrance opening 17 formed therein for receiving waste material to be heated in the gravity drop steam heating tower 13, and a lower end portion 19 having an exit opening 21 formed therein for discharging the waste material that has been treated in the gravity drop steam heating tower 13. The gravity drop steam heating tower 13 preferably is cylindrically shaped and oriented vertically, and preferably has a five foot diameter and a height of twelve feet. However, the dimensions of the gravity drop steam heating tower 13 may be varied as desired, to accommodate desired through-put of waste material to be treated by the apparatus 11.

Figure 1:
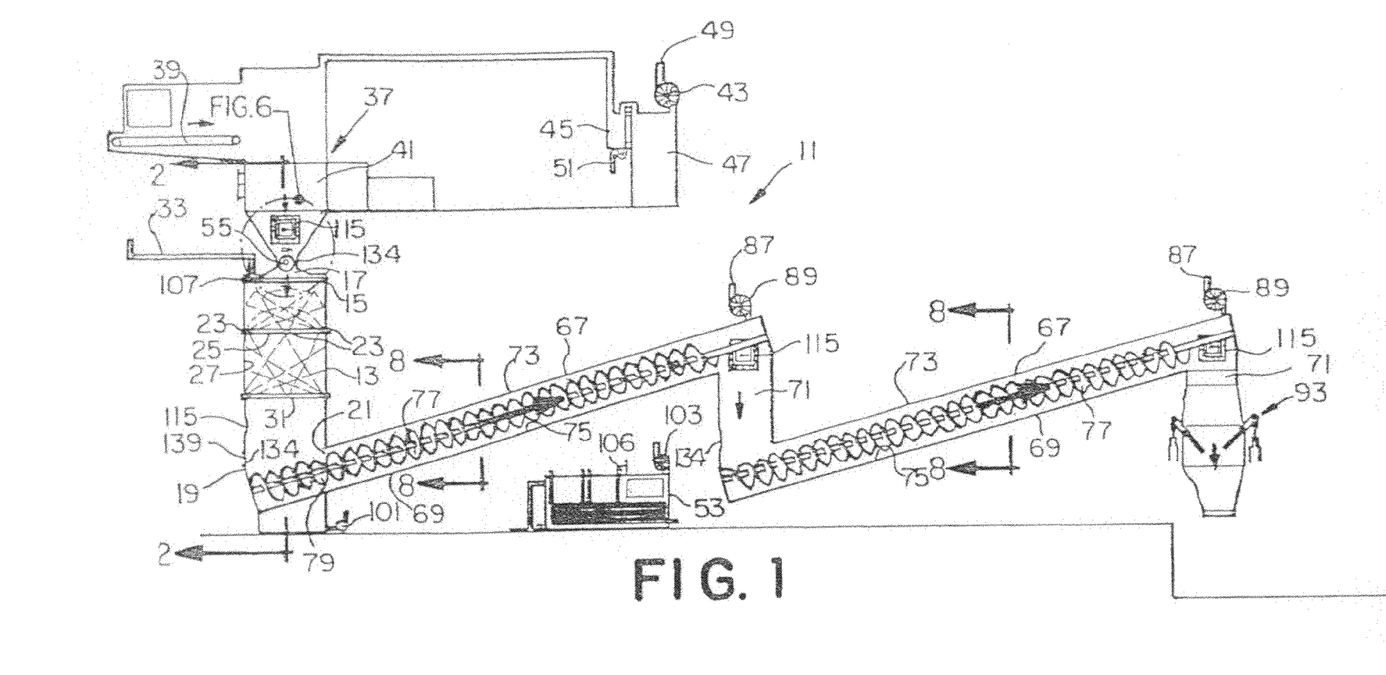
FIG. 1 is a schematic front sectional view of a preferred waste treatment apparatus constructed in accordance with the invention.
Figure 2:
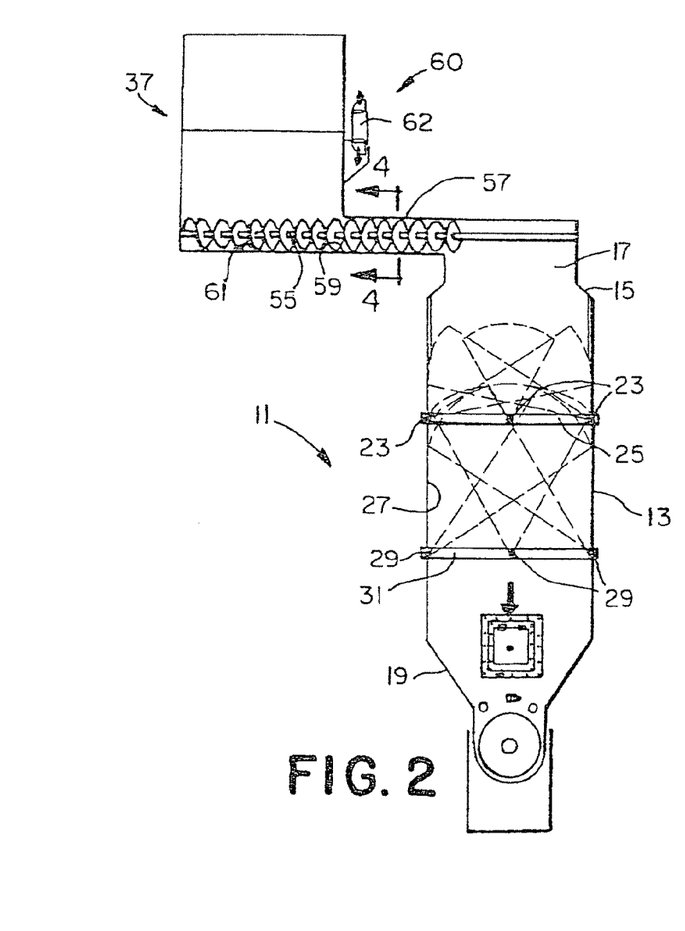
FIG. 2 is a schematic cross-sectional view along the lines and arrows 2-2 in FIG. 1.
Figure 3:
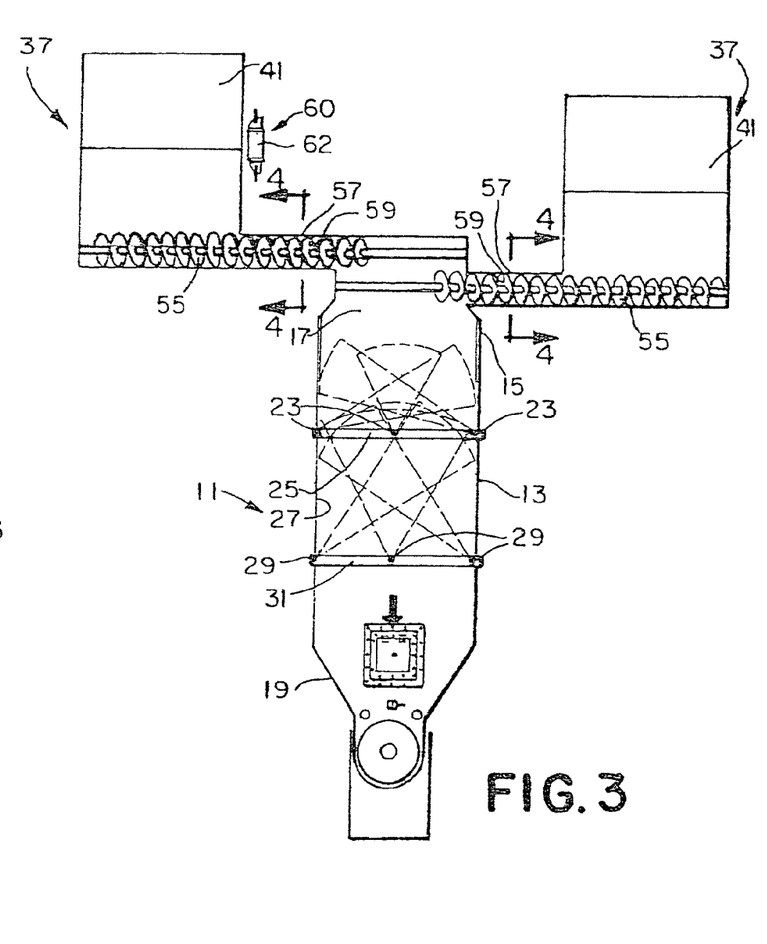
FIG. 3 is a schematic cross-sectional view showing the gravity drop steam heating tower 13 and two feed hoppers 37 each having an integral shredder 41 and a feed member 55 for feeding waste material to the gravity drop steam heating tower 13 in an alternative embodiment of the invention.

Mounted inside the gravity drop steam heating tower 13 is a steam nozzle system that is provided to directly impact the waste material being treated in the gravity drop steam heating tower 13 with steam and to promote the circulation of waste material in the gravity drop steam heating tower 13 to facilitate rapidly heating the waste material to a temperature (preferably 210 degrees Fahrenheit±4 degrees Fahrenheit) sufficient to kill the pathogens in the waste material. The steam nozzle system may include a plurality of nozzles located at various heights and positioned in various directions to accommodate the size of the gravity drop steam heating tower. Preferably, as shown in FIGS. 1-3, the steam nozzle system includes a first set of steam nozzles 23 mounted along and communication with a steam conduit 25 positioned along the interior wall 27 of the gravity drop steam heating tower 13 at about a distance of one third of the distance between the upper end portion 15 of the gravity drop steam heating tower 13 and the lower end portion 19 of the gravity drop steam heating tower 13 down from the upper end portion 15 of the gravity drop steam heating tower 13. The steam conduit 25 is connected to a steam source (not shown) for supplying steam to the steam conduit 25. Preferably, the nozzles 23 are angled upwardly and toward the center axis of the gravity drop steam heating tower at an angle of 22°±4°. Pressurized steam sprayed from the nozzles 23 tends to separate and spread the waste material entering the gravity drop steam heating tower 13.

Preferably, as shown in FIGS. 1-3, the steam nozzle system includes a second set of steam nozzles 29 mounted along and in communication with a steam conduit 31 positioned along the interior wall 27 of the gravity drop steam heating tower 13 at about a distance of two thirds of the distance between the upper end portion 15 of the gravity drop steam heating tower 13 and the lower end portion 19 of the gravity drop steam heating tower 13 down from the upper end portion 15 of the gravity drop steam heating tower 13. The steam conduit 31 is connected to a steam source (not shown) for supplying steam to the steam conduit 31. Preferably, the nozzles 29 are angled upwardly and toward the center axis of the gravity drop steam heating tower at an angle of 45°±10°. Pressurized steam from the nozzles 29 tends to suspend the waste material particles and promote circulation of the waste material in the gravity drop steam heating tower 13, while rapidly raising the temperature of waste material particles.

The gravity drop steam heating tower 13 has a pressure equalization vent 33 to prevent the gravity drop steam heating tower 13 from becoming over-pressurized with steam.

Preferably, the gravity drop steam heating tower 13 also is provided with access doors to permit inspection and service of the gravity drop steam heating tower 13. The access doors are provided with a seal to prevent steam from leaking from the access doors during use of the gravity drop steam heating tower 13.

As shown in FIGS. 1-3, preferably a feed hopper 37 is provided which receives waste material to be treated by the waste treatment apparatus 11. Also, as shown in FIG. 1, a material handling system 39 preferably is provided to feed the waste material to be treated by the waste treatment apparatus 11 to the feed hopper 37. Although the material handling system 39 shown in the drawings is a conveyor, the material handling system 39 may be comprised of a conveyor or conveyors, an elevator or elevators, a tipper or tippers, a dumper or dumpers, or a combination thereof as may be appropriate for the waste material being treated. The waste handling system 39 may use any combination of material handling equipment to accommodate variations in the waste material packaging or transportation systems.

Preferably, a shredder 41 is provided to shred the waste material to a desired particle size. The shredder 41 preferably is integral with the feed hopper 37 and comprises a combination of cutters and sizing screen such that the waste material at a desired particle size falls by gravity from the shredder 41 to the lower end portion of the feed hopper 37. However, if the waste material to be treated does not require shredding by the waste treatment apparatus 11 (e.g., when the waste material has been pre-shredded prior to being fed into the waste treatment apparatus 11), the shredder 41 may be omitted from the waste treatment apparatus 11.

Alternatively, more than one feed hopper 37 may be provided for receiving waste material to be treated by the waste treatment apparatus 11, and when more than one feed hopper 37 is provided, preferably each feed hopper 37 its own feed member 55 for feeding the waste material in the hopper 37 to the gravity drop steam heating tower 13. Also, each feed hopper 37 preferably has a shredder 41 that is integral with it, and its own material handling system 39 for feeding the waste material to be treated by the waste treatment apparatus 11 to the feed hopper 37. The ability to accommodate different size reduction requirements which may be associated with certain material waste streams (e.g., sharps in regulated medical waste streams) may be accomplished by providing multiple shredders 41, whereby the waste material is divided by type and fed to a shredder 41 dedicated to shredding that type of medical waste. Also, providing multiple feed hoppers 37/shredders 41 permits the shredding capacity to be increased and/or permits maintenance to be done on at least one of the feed hoppers 37/shredders 41 (not every feed hopper 37/shredder 41 of the waste treatment apparatus 11 simultaneously), without completely shutting down the operation of the waste treatment apparatus 11. An example of the waste apparatus 11 having multiple feed hoppers 37/shredders 41 is shown in FIG. 3 where the waste treatment apparatus 11 is provided with two sets of a feed hopper 37 and shredders 41.

The material handling system 39, the shredder 41, and the feed hopper 37 are all maintained under negative air pressure through a de-misting and a high efficiency particulate air (HEPA) filter system during use of the waste treatment apparatus 11. The air in the material handling system 39, the shredder 41, and the feed hopper 37 is drawn off by a fan 43 through the de-misting filter 45 to condensate entrained mist and then through HEPA filters 47 to collect any airborne pathogens. The fan 43 discharges clean air to the atmosphere through a vent 49. The de-misting filter 45 is provided with a drain line 51 for feeding liquid condensate contained therein to a waste water evaporator 53 (which is described below), to a sanitary sewer where permitted, or to a holding tank.

Figure 4:
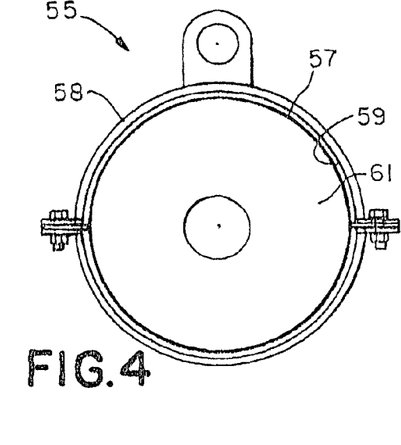
FIG. 4 is a schematic cross-sectional view taken along the lines and arrows 4-4 shown in FIGS. 2 and 3.
Figure 5:
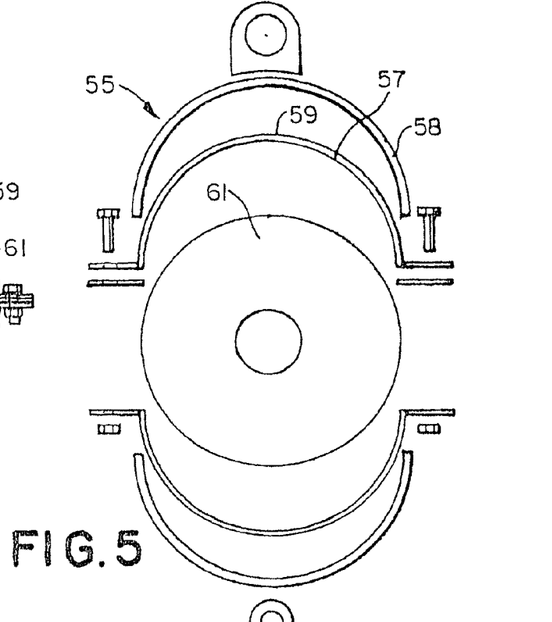
FIG. 5 is an exploded view of the schematic view shown in FIG. 4.

A feed member 55 is provided at the bottom end portion of the feed hopper 37 for feeding the waste material to the gravity drop steam heating tower 13, and preferably is configured to provide a seal between the feed hopper 37 and the gravity drop steam heating tower 13 to prevent steam from escaping from the gravity drop steam heating tower 13 through the feed hopper 37. A preferred example of the feed member 55, shown in FIGS. 1-6, comprises a screw conveyor having an elongated enclosure 57 (preferably having a length greater than or equal to 36 inches) having a cylindrical inner wall 59, and a helical screw or auger 61 extending through the elongated enclosure 57 for moving the shredded waste material from the bottom of the feed hopper 37 to the entrance opening 17 of the gravity drop steam heating tower 13. The auger 61 preferably fits into the enclosure 57 with a small clearance between its blade and the cylindrical inner wall 59 of the enclosure 57. Preferably, the auger 61 is rotated by a chain (not shown) driven by a motor (not shown). As shown in FIGS. 2, 3, and 4, the feed member 55 when filled with waste material creates a seal between the feed hopper 37 and the gravity drop steam heating tower 13 to prevent steam from escaping from the gravity drop steam heating tower 13 through the feed hopper 37. The elongated enclosure 57 preferably is provided with insulation 58 to retain heat.

Figure 7:
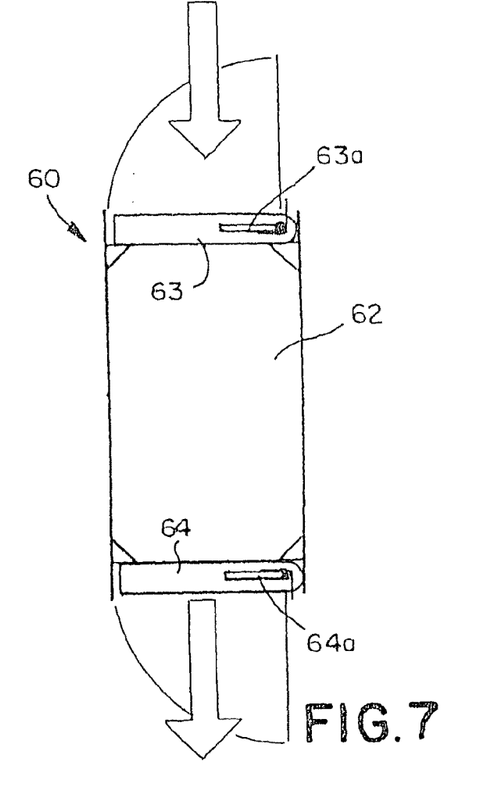
FIG. 7 is a schematic view in side elevation of the chambered port 60.

A chambered port 60, shown in FIGS. 2, 3, and 7, is connected to the lower end portion of the feed hopper 37 to allow for the introduction of challenge testing material (such as spore tests) to the waste treatment apparatus 11 to verify the efficacy of the waste treatment apparatus 11 by examining the challenge testing material after it has been processed in the waste treatment apparatus 11. The port 60 preferably is chambered to allow the introduction of the challenge testing material to the waste stream while preventing the release of airborne pathogens to the work environment when the challenge testing material is introduced into the waste treatment apparatus 11. The chambered port 60 comprises a sealed chamber 62 having a spring-loaded door 63 closing the chamber 62 from the work environment outside the waste treatment apparatus 11, and a second spring-loaded door 64 closing the chamber 62 from the interior of the feed hopper 37. When it is desired to introduce challenge testing material to the waste treatment apparatus 11, the spring loaded door 63 may be pulled open using an activation lever 63a and the challenge testing material placed in the chamber 62. Then, the door 63 may be allowed to close. After the door 63 has closed, the door 64a may be opened using an activation lever 65, resulting in the challenge testing material falling due to gravity into the waste stream in the lower end portion of the feed hopper 37. Because insertion of challenge testing material through the chambered port 60 bypasses the shredder 41, the challenge testing material is not destroyed by the cutting blades of the shredder 41. After the challenge testing material has been added to the waste stream, the door 64 may be allowed to close. Since the door 63 is in a closed position when the challenge waste material is added to the waste stream through door 64, the door 63 blocks the release of airborne pathogens from the lower end portion of feed hopper 37 into the work environment when the challenge testing material is added to the waste stream.

Preferably, the feed hopper 37 is also provided with access doors to permit inspection and service of the feed hopper 37. The access doors are provided with a seal to prevent the waste material from leaking from the access doors during use of the waste treatment apparatus 11.

A vaporization system 67 is provided for increasing the temperature and thermal energy level of the waste stream moving through the vaporization system 67 to facilitate the vaporization of liquids in the waste stream after the waste stream has been treated in the gravity drop steam heating tower 13. The vaporization system 67 also provides for sufficient retention time of the waste material at or above the biological kill temperature.

The vaporization system 67 includes a heating chamber 69 for providing additional heat to the waste stream by conduction to heat the waste stream to a temperature sufficient to promote vaporization of liquids entrained in the waste stream, and a vaporization chamber 71 into which the waste stream from the heating chamber 69 is fed where the vapor entrained in the waste stream is released and drawn out of the vaporization chamber 71 to produce a drier waste material.

Figure 8:
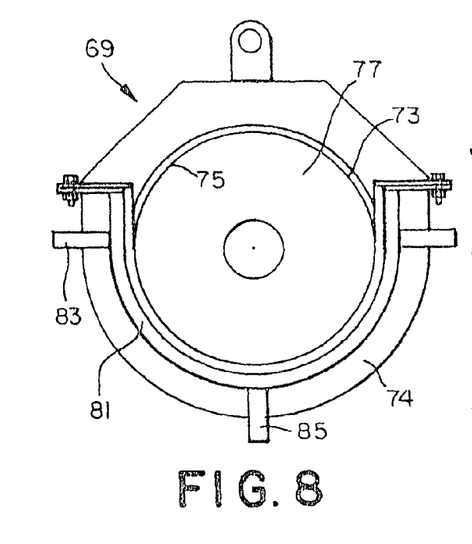
FIG. 8 is a schematic cross-sectional view taken along the lines and arrows 8-8 shown in FIG. 1.

The heating chamber 69 preferably is configured to provide a seal between the vaporization chamber 71 and the gravity drop steam heating tower 13. A preferred example of the heating chamber 69, shown in FIGS. 1, 8, and 9, comprises a screw conveyor having an elongated enclosure or enclosed trough 73 having a cylindrical inner wall 75, and a helical screw or auger 77 extending through the enclosed trough 73 for moving the waste material from the lower end portion 19 of the gravity drop steam heating tower 13 to the entrance opening 79 of the vaporization chamber 71. The auger 77 preferably fits into the enclosed trough 73 with a small clearance between its blade and the cylindrical inner wall 75 of the enclosed trough 73. Preferably, the auger 77 is rotated by a chain (not shown) driven by a motor (not shown). As shown in FIG. 8, the heating chamber 69, when filled with waste material, creates a seal between the vaporization chamber 71 and the gravity drop steam heating tower 13. The length of heating chamber 69 and the speed of the auger 77 provide sufficient retention time of the waste material in the vaporization system(s) 67 such that the waste material is subjected to a temperature at or above the biological kill temperature for a sufficient amount of time before processing in the waste treatment apparatus 11 is completed.

Figure 9:
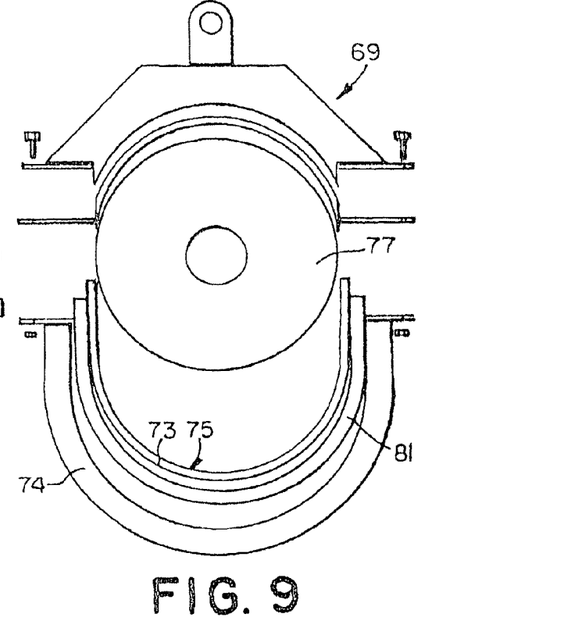
FIG. 9 is an exploded view of the heating chamber 69 shown in FIG. 8.

In the preferred embodiment shown in the drawings, the enclosed trough 73 is provided with a steam chamber 81 along its length and the lower 180° of its circumference. Preferably, the steam chamber 81 maintains steam contained therein at a pressure of about 15 to 17 psi, which corresponds to a steam temperature of about 250° to 267° Fahrenheit. The enclosed trough 73 preferably is provided with insulation 74 to retain heat and to protect workers from being burned if the outside of the heating chamber 69 is touched. As the waste material is conveyed by the auger 77 through the heating chamber 69, the temperature of the waste material is increased by conduction to a temperature sufficient to vaporize liquids entrained in the waste material (preferably to 230° to 250° Fahrenheit), before it falls by gravity into the vaporization chamber 71. The steam chamber 81 is fitted with a steam inlet 83, which receives steam from a steam line (not shown), and a steam trap drainage system 85, which feeds to a condensate return or a drain. Preferably, the heating chamber 69 is provided with access doors to permit inspection and service of the heating chamber 69, and the access doors are sealed during use of the heating chamber 69.

In the embodiment of the invention shown in the drawings, two vaporization systems 67 are provided in series. However, the number of vaporization systems 67 used may be one, two, three or more as desired, in response to variables such as what capacity of waste is desired to be processed through the waste treatment apparatus 11 and/or what degree of dryness is desired to be obtained for the processed waste. Typically, an apparatus 11 having two vaporization chambers 67 processes up to 3,000 pounds of waste material per hour and an apparatus 11 having three vaporization chambers 67 processes up to 5,000 pounds of waste material per hour.

The vaporization chamber 71 of each vaporization system 67 receives heated waste material from the heating chamber 69. The vaporization chamber 71 is provided with a vent 87 and a vaporization vent fan 89 in communication therewith for producing a negative pressure in the vaporization chamber 71 to promote flash off of moisture from the heated waste material conveyed into the vaporization chamber 71 from the heating chamber 69 and removal of vapors from the vaporization chamber 71 conveyed in the waste material received from the heating chamber 69. The vapor is drawn from the vaporization chamber 71 by the vaporization vent fan 89 and released to the atmosphere. By removing vapors entrained in the waste material and flashing off moisture from the waste material, the waste material in the vaporization chamber 71 becomes drier. The vaporization chamber 71 also is provided with access doors to permit inspection and service of the vaporization chamber 71.

Figure 11:
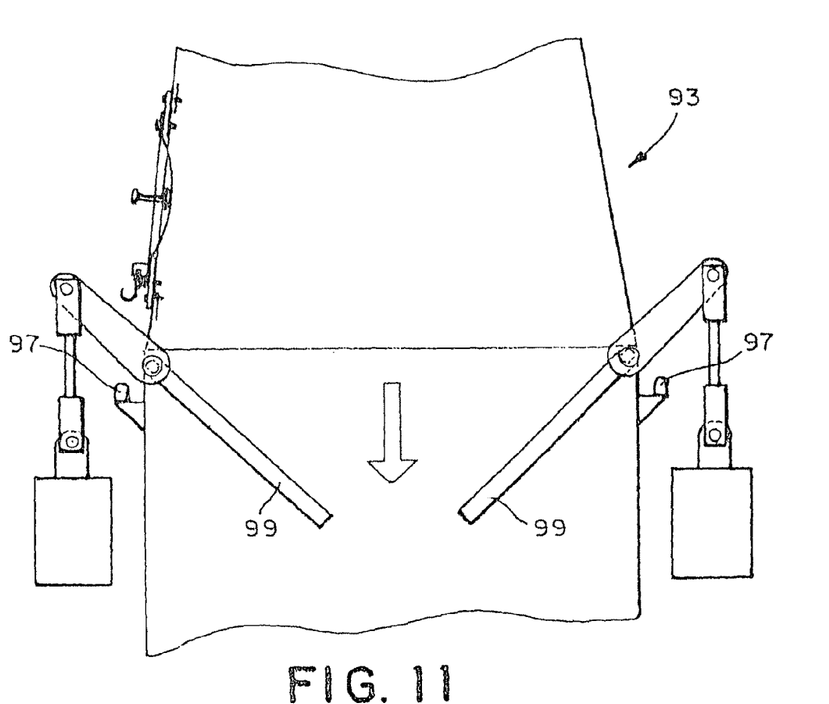
FIG. 11 is an enlarged schematic view in cross-section of the door 93.

Waste treatment apparatus 11 is provided with a door 93 mounted on the last vaporization chamber 71 of the waste treatment apparatus 11 through which the waste material treated by the waste treatment apparatus 11 is discharged from the waste treatment apparatus 11, preferably into a processed waste container. Accordingly, in the illustrative example shown in the drawings, the door 93 is provided on the second vaporization chamber 71. Preferably, door 93 comprises an adjustable counterbalance clamshell-type door. The door 93 holds the processed material in the last vaporization chamber 71 to facilitate the removal of vapor by the vaporization fan 89, and the door 93 preferably is adjusted to open to release the processed waste material from the last vaporization chamber 71 when a certain weight of processed waste material has accumulated in the last vaporization chamber 71. In the preferred embodiment of the invention shown in the drawings, the door 93 opens when the weight of the processed materials accumulated in the vaporization chamber 71 on the door 93 outweighs the weight of the counterbalance weights 95 of the door 93. Preferably, door 93 is also provided with rotational stops 97 to prevent the door panels 99 from moving upwardly past the horizontal position.

Figure 10:
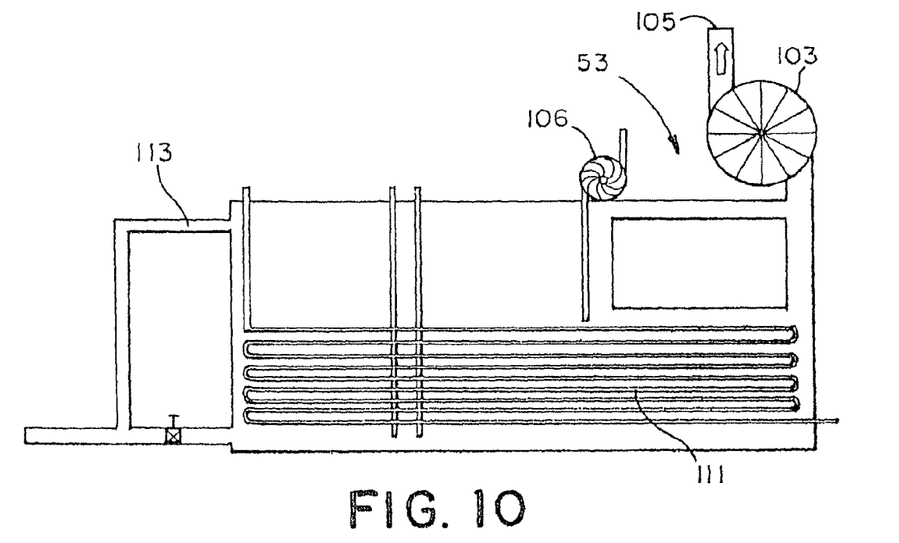
FIG. 10 is a schematic view shown in partial section of the waste water evaporator 53.

Optionally, but preferably, the waste water evaporator 53 is provided, which collects excess waste water pumped or gravity fed from the drain line 51 and a sump 101 provided in the lower end portion 19 of the gravity drop steam heating tower 13. The waste water collected in the waste water evaporator 53 is heated to the point of vaporization (at least 212° Fahrenheit) and the resultant sterile vapor is drawn off by a vaporization fan 103 through a vent 105 to the atmosphere. Additionally, hot water preferably is drawn off the waste water evaporator 53 by a pump 106 to provide hot water (preferably 212 degrees Fahrenheit) to a hot water spray down system 107 located in the interior of the gravity drop steam heating tower 13 in its upper end portion 15. The hot water spray down system 107 comprises a wash down spray ring 109 into which the hot water from the waste water evaporator 53 flows and from which hot water is discharged down the interior wall 27 of the gravity drop steam heating tower 13 to clean the interior wall 27 of the gravity drop steam heating tower 13, when desired. The waste water evaporator 53 is provided with access doors to provide inspection and service of the waste water evaporator 53. A steam-based heat exchanger 111 which receives steam from a steam supply line is used to heat and evaporate the waste water collected in the waste water evaporator 53. The waste water evaporator 53 also is provided with an overflow line 113 if too much waste water is collected in the evaporator 53 before evaporation therein occurs, and the overflow line 113 leads to a sanitary sewer or a holding tank.

If the waste water evaporator 53 is omitted from the waste treatment apparatus 11, the waste water collected from the drain line 51 and the sump 101 may be routed to a sanitary sewer where permitted, or to a holding tank. If the waste water evaporator 53 is omitted from the waste treatment apparatus 11, the spray down system 107 may be provided with an alternative source for hot water to be used to clean the interior of the gravity drop steam heating tower 13.

The lower end portion of the feed hopper 37, the lower end portion 19 of the gravity drop steam heating tower 13, and the vaporization chamber(s) 71 act as surge areas designed to accommodate the variations in density of flow of the waste stream.

Figure 12:
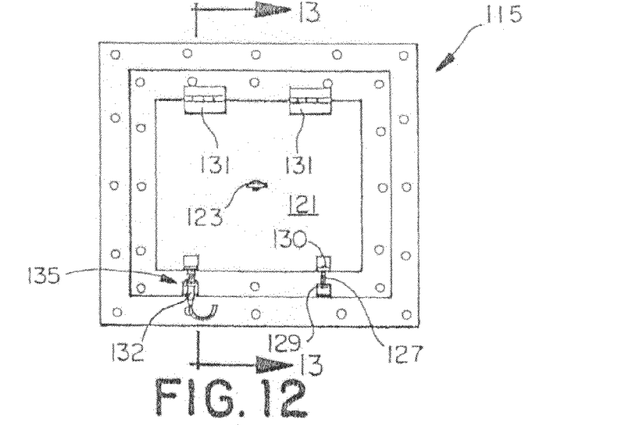
FIG. 12 is a schematic view in front elevation of a surge area pressure monitor 115.
Figure 13:
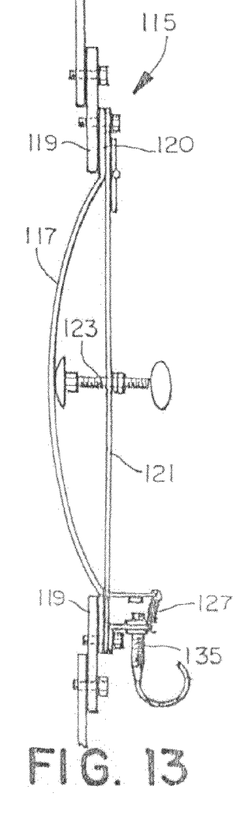
FIG. 13 is a schematic view in cross section of the surge area pressure monitor 115 taken along the lines and arrows 13-13 of FIG. 12.
Figure 14:
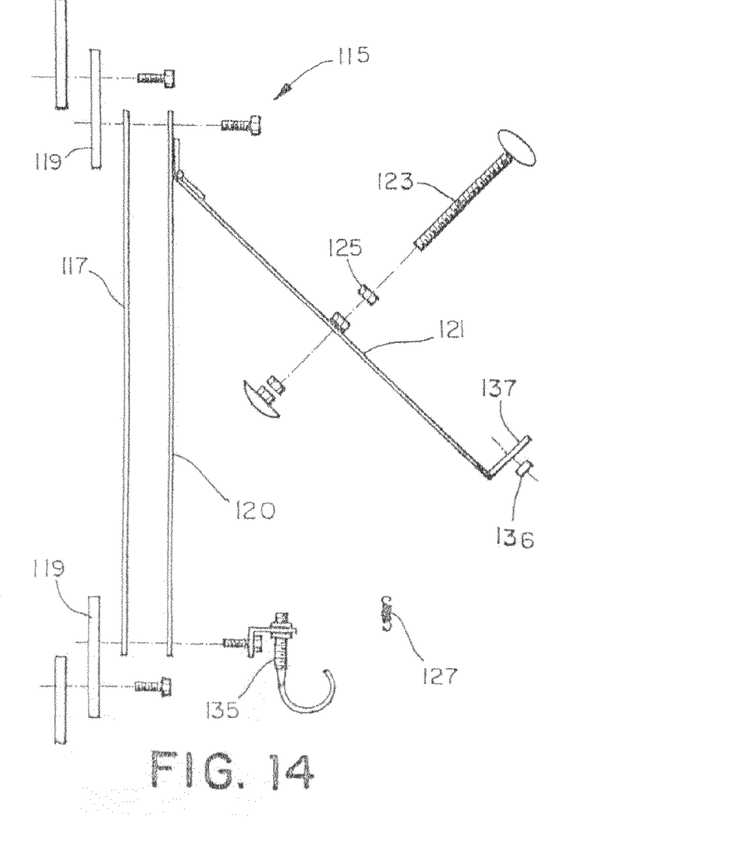
FIG. 14 is an exploded view of the surge area pressure monitor 115 shown in FIG. 13.

In order to prevent the surge areas from overfilling with waste material, an adjustable surge pressure monitor 115 is provided at each of these areas. The surge areas are designed to accommodate a sufficient volume of waste material to facilitate a regular flow through the waste treatment apparatus 11. The adjustable surge pressure monitor 115 is self contained, and includes a flexible membrane 117 that provides a barrier between the surge area and the ambient environment. The membrane 117 is mounted between a pair of frames 119, 120. A hinged, flush fitting stainless steel door 121 having hinges 131 is fitted onto the frame 120 next to the membrane 117 and is provided with an adjustable length plunger 123 which is held at the desired length by locknuts 125. The door 121 is held closed by an extension spring 127 mounted between a tab 129 mounted on the frame 120 and a tab 130 formed on the door 121. The position status of the door 121 is communicated to a controller 133, via an adjustable inductive proximity sensor 135, which is mounted on a tab 132 mounted on the frame 120. The sensor 135 monitors the presence of a small piece of ferrous material 136 mounted on a tab 137 of the door 121. The length of the plunger 123 is adjusted to abut against the membrane 117 causing the membrane 117 to bulge into the surge area, and the spring tension of the spring 127 is adjusted to provide sufficient tension to hold the door 121 closed with the plunger 123 abutting the membrane 117. When the surge area approaches becoming overfull, the surge pressure created thereby in the surge area pushes against the membrane 117 forcing the membrane 117 to move outwardly from the surge area overcoming the spring tension applied by the spring 127 and pushing the door 121, via the plunger 123, open. When the door 121 is pushed slightly open by the surge pressure created in the surge area as the surge area approaches becoming overfull, the sensor 135 signals the controller 133 of the condition, which initiates a signal to commence moving the waste material in the surge area further downstream in the waste treatment apparatus 11. The tension of the spring 127 closes the door 121 automatically as the surge pressure in the surge area is relieved due to waste material being moved from the surge area for further processing in the waste treatment apparatus 11, causing the plunger 123 to push against the membrane 117 to cause the membrane 117 again to bulge into the surge area. The closing of the door 121 automatically resets the sensor 135 and its signal to the controller 133 to the normal position indicating that the surge area is no longer at a level approaching becoming overfull. While the monitor 115 preferably is held together with bolts or screws for ease of service, it may be mounted to the surge area wall by welding, if desired.

Figure 6:
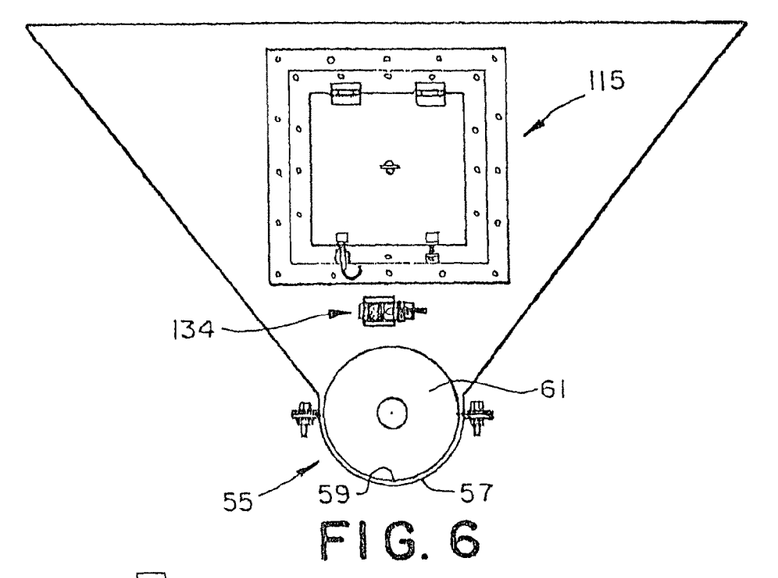
FIG. 6 is an enlarged view of the surge area pressure monitor 115, the level sensor 134, and the auger 61 shown in the circle 6 in FIG. 1.

Level sensors 134, preferably laser-based or fiber optic-based, in communication with the controller 133, are provided at various locations (e.g., in the surge area in the feed hopper 37 at the front end of auger 61, in the surge area in the gravity drop steam heating tower 13 at the front end of auger 77, and in the surge area in the first vaporization chamber 71 at the front end of the auger 77 of the second vaporization system 67 in the illustrative example of the invention shown in the drawings) to sense the level of waste material enabling the controller 133 to stop rotation of the auger at any of the sensors 134 if the level of accumulated waste material drops too low at the front end of an auger 50 as to keep that auger filled with material waste to maintain a seal therewith.

Figure 15:
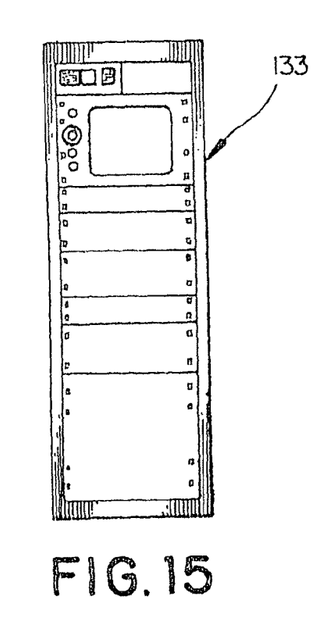
FIG. 15 is a view in front elevation of the controller 133.

The controller 133, which may be a conventional microprocessor-based controller and, preferably, is a programmable logic controller (PLC) having appropriate programming installed therein, regulates the operation of the waste treatment apparatus 11.

Preferably, the controller 133 includes a user interface to provide real time viewing of process parameters and system conditions. The controller 133 preferably is provided with ethernet capabilities to allow remote real time viewing of process parameters as well as access to available reports. Temperature sensors may be placed at surge areas and along the length of each vaporization system 67 to stream temperature data to the controller 133.

The controller 133 controls material handling speeds, auger speeds, and steam flow to accomplish an efficient combination of sterilization and production rate. The waste treatment apparatus 11 via the controller 133 maintains a history of temperature and auger speed trends which may be accessed by authorized personnel and maintained for regulatory compliance.

A steam pressure sensor, in communication with the controller 133, may be fitted to the main steam supply line to ensure that appropriate steam pressure is available to operate the waste treatment apparatus 11. Sensor inputs of varying types and purposes, such as sensor inputs 139, and the controller 133 programming combine to provide a self-diagnosing system of critical and non-critical faults. Non-critical "system flow" faults are generally automatically corrected, as the controller 133 sub-systems are programmed to clear bottlenecks in the waste treatment apparatus 11, and may automatically pause and restart production, as needed. The user interface may display non-critical fault status and the action(s) automatically taken to correct the fault. The controller 133 is programmed to stop production when critical faults are recognized by the controller 133, and such critical faults, along with suggestions for correction, are communicated to the operator of the waste treatment apparatus 11 via an operator interface.

In use, waste material to be treated in the waste treatment apparatus 11 of the invention is feed into the gravity drop steam heating tower 13, where the waste material is heated to a biological kill temperature using pressurized steam at preferably 15 to 17 psi that is sprayed onto the waste material particles as they fall through the gravity drop steam heating tower 13.

Preferably, the waste material is conveyed to the feed-hopper 37 using the material handling system 39, and the waste material is shredded using the shredder 41.

The shredded waste material is conveyed from the feed hopper 37 to the gravity drop steam heating tower 13 preferably using the feed member 55, and the rotation speed of the auger 61 of the feed member 55 is controlled by the controller 133 to control the rate of flow of waste material into the gravity drop steam heating tower 13 and to ensure that the auger 61 is filled with waste material during operation in order to create a seal between the feed hopper 37 and the gravity drop steam heating tower 13 to prevent steam from escaping from the gravity drop steam heating tower 13 through the feed hopper 37.

As the waste material falls by gravity through the gravity drop steam heating tower 13, the pressurized steam sprayed inside the gravity drop steam heating tower 13 rapidly raises the temperature of the waste material particles to the biological kill temperature for killing pathogens.

After treatment in the gravity drop steam heating system 13, the waste material is transported by the auger 77 into the heating chamber 69, where the waste material is heated by conduction to a temperature (preferably 230 degrees to 250 degrees Fahrenheit) to facilitate vaporization of liquids entrained in the waste material.

The heated waste material exits the heating chamber 69 and falls by gravity into the vaporization chamber 71, where vapor from the waste material is released and removed from the vaporization chamber 71, resulting in a drier waste material. In the preferred embodiment of the invention shown in the drawings, the waste material is fed from the vaporization chamber 71 of the first vaporization system 67 into the heating chamber 69 of the second vaporization system 67 using the auger 77 of the second vaporization system 67 where the waste material again is heated by conduction to temperatures sufficient to vaporize liquids entrained in the waste material (preferably 230 degrees to 250 degrees Fahrenheit). The waste material then falls by gravity from the heating chamber 69 of the second vaporization system 67 into the vaporization chamber 71 of the second vaporization system 67, where vapor from the waste material is released and removed from the vaporization chamber 71, resulting in an even drier waste material.

The resultant waste material accumulates on the door 93 at the exit of the vaporization chamber 71 of the second vaporization system 67 until the weight of the accumulated waste material resting on the door 93 outweighs the counterbalance weight of the door 93 resulting in the door 93 opening to discharge the treated waste material from the waste treatment apparatus 11, preferably into a processed waste container.

The example of the process of the invention set out above is based on a waste treatment apparatus 11 having two vaporization systems 67 arranged serially one after the other. However, if longer retention times are desired, additional vaporization systems 67 may be added in a serial arrangement, with the last vaporization system 67 being provided with the door 93.

In a preferred embodiment of the invention, the operation of the waste treatment apparatus 11 is controlled by the controller 133. The controller 133 controls material handling speeds, auger speeds, and steam flow to accomplish an efficient combination of sterilization and production. The controller 133 monitors the negative air system for appropriate operation and pressure differential across the HEPA filters. The controller 133 also monitors the surge areas with the monitors 115 and level sensors 134 to ensure that the surge areas do not become overfull or underfilled and to control auger speed rates to ensure that each auger of the apparatus 11 has sufficient waste material carried thereby to create a seal.

The invention claimed is:

1. An apparatus for treating waste, comprising
    a gravity drop steam heating tower for heating the waste to the biological kill temperature using pressurized steam, the gravity drop steam heating tower having an interior, an upper end portion, and a lower end portion,
    a first feed member for feeding the waste to be sterilized to the gravity drop steam heating tower, and
    a first vaporization system, the first vaporization system including
    (a) a heating chamber for facilitating vaporization of liquids in the waste, the heating chamber including a conveying member for conveying the waste from the lower end portion of the gravity drop steam heating tower into and through the heating chamber, and
    (b) a vaporization chamber for receiving the waste from the heating chamber and for releasing vapor entrained in the waste into the vaporization chamber,
    and the apparatus further including
    at least another feed member, in addition to first feed member, for feeding the waste to be sterilized to the gravity drop steam heating tower, and
    a plurality of hoppers from which the feed members draw the waste material to be sterilized, each feed member having a counterpart hopper.

2. The apparatus of claim 1,
each hopper having a shredder positioned upstream of its exit port for shredding the waste.

3. The apparatus of claim 1,
each feed member being a screw conveyor for conveying the waste material from its counterpart hopper to the gravity drop steam heating tower and for creating a steam seal between the hopper and the gravity drop steam heating tower with the waste material being conveyed.

4. The apparatus of claim 1, further including
a controller in communication with each feed member for controlling flow of waste material into the gravity drop steam heating tower.

5. An apparatus for treating waste, comprising
a gravity drop steam heating tower for heating the waste to the biological kill temperature using pressurized steam, the gravity drop steam heating tower having an interior, an upper end portion, and a lower end portion,
a first feed member for feeding the waste to be sterilized to the gravity drop steam heating tower, and
a first vaporization system, the first vaporization system including
(a) a heating chamber for facilitating vaporization of liquids in the waste, the heating chamber including a conveying member for conveying the waste from the lower end portion of the gravity drop steam heating tower into and through the heating chamber, and
(b) a vaporization chamber for receiving the waste from the heating chamber and for releasing vapor entrained in the waste into the vaporization chamber,
the gravity drop steam heating tower having an upper end portion, a lower end portion, a distance between the upper end portion and the lower end portion, a central axis extending between the upper end portion and the lower end portion, an interior, an interior wall, and steam nozzles positioned in the interior for bringing steam into direct contact with the waste material in tower, and
the steam nozzles including a first set of spaced apart steam nozzles positioned along the interior wall at about a distance of one-third of the distance between the upper end portion of the gravity drop steam heating tower and the lower end portion of the gravity drop steam heating tower down from the upper end portion of the gravity drop steam heating tower, the steam nozzles of the first set of steam jets being angled upwardly and toward the center axis of the gravity drop steam heating tower at an angle of 22 degrees ±4 degrees, and
the steam nozzles including a second set of spaced apart steam nozzles positioned along the interior wall at about a distance of two-thirds of the distance between the upper end portion of the gravity drop steam heating tower and the lower end portion of the gravity drop steam heating tower down from the upper end portion of the gravity drop steam heating tower, the steam jets of the first set of steam jets being angled upwardly and toward the center axis of the gravity drop steam heating tower at an angle of 45 degrees ±10 degrees.

6. The apparatus of claim 5, further including
a hopper from which the first feed member draws the waste to be sterilized.

7. The apparatus of claim 6, further including
a material handling system positioned upstream of the hopper for feeding the waste to be sterilized to the hopper.

8. The apparatus of claim 5, including
a shredder positioned upstream of the gravity drop steam heating tower for shredding the waste to be sterilized.

9. The apparatus of claim 5,
the conveying member being a screw conveyor that creates a seal between the gravity drop steam heating tower and the vaporization chamber.

10. The apparatus of claim 5, further including
a controller for controlling operation of the waste treatment apparatus.

11. The apparatus of claim 10,
the controller being in communication with a steam feed line for feeding steam to the gravity drop steam heating tower for controlling flow of steam to the gravity drop steam heating tower.

12. The apparatus of claim 10, further including
a material handling system for feeding the waste to be sterilized to the apparatus,
the controller being in communication with the material handling system for controlling flow of the waste material to be sterilized into the apparatus.

13. The apparatus of claim 10,
the controller being in contact with the conveying member for controlling flow of waste material from the gravity drop steam heating tower into and through the heating chamber of the first vaporization system.

14. An apparatus for treating waste, comprising
a gravity drop steam heating tower for heating the waste to the biological kill temperature using pressurized steam, the gravity drop steam heating tower having an interior, an upper end portion, and a lower end portion,
a first feed member for feeding the waste to be sterilized to the gravity drop steam heating tower, and
a first vaporization system, the first vaporization system including
(a) a heating chamber for facilitating vaporization of liquids in the waste, the heating chamber including a conveying member for conveying the waste from the lower end portion of the gravity drop steam heating tower into and through the heating chamber, and
(b) a vaporization chamber for receiving the waste from the heating chamber and for releasing vapor entrained in the waste into the vaporization chamber,
the apparatus further including
a hopper from which the first feed member draws the waste to be sterilized,
the first feed member being a screw conveyor for conveying the waste material from the hopper to the gravity drop steam heating tower and for creating a steam seal between the hopper and the gravity drop steam heating tower with the waste material being conveyed.

15. An apparatus for treating waste, comprising
a gravity drop steam heating tower for heating the waste to the biological kill temperature using pressurized steam, the gravity drop steam heating tower having an interior, an upper end portion, and a lower end portion,
a first feed member for feeding the waste to be sterilized to the gravity drop steam heating tower, and
a first vaporization system, the first vaporization system including
(a) a heating chamber for facilitating vaporization of liquids in the waste, the heating chamber including a conveying member for conveying the waste from the lower end portion of the gravity drop steam heating tower into and through the heating chamber, and (b) a vaporization chamber for receiving the waste from the heating chamber and for releasing vapor entrained in the waste into the vaporization chamber, the heating chamber having a length, an upper half, and a lower half, the heating chamber having an interior wall and a steam chamber in contact with at least a portion of the interior wall for heating the interior wall and the waste material being conveyed through the heating chamber by conduction.

16. The apparatus of claim 15, the steam chamber extending along the length of the heating chamber and the lower half of the heating chamber.

17. The apparatus of claim 15, further including a controller in communication with a steam feed line for feeding steam to the steam chamber for controlling flow of steam to the steam chamber.

18. An apparatus for treating waste, comprising a gravity drop steam heating tower for heating the waste to the biological kill temperature using pressurized steam, the gravity drop steam heating tower having an interior, an upper end portion, and a lower end portion, a first feed member for feeding the waste to be sterilized to the gravity drop steam heating tower, and a first vaporization system, the first vaporization system including (a) a heating chamber for facilitating vaporization of liquids in the waste, the heating chamber including a conveying member for conveying the waste from the lower end portion of the gravity drop steam heating tower into and through the heating chamber, and (b) a vaporization chamber for receiving the waste from the heating chamber and for releasing vapor entrained in the waste into the vaporization chamber, the vaporization chamber having a vaporization vent and a vaporization vent fan in communication therewith for producing a negative pressure in the vaporization chamber to promote flash off of moisture and removal of vapors from the vaporization chamber conveyed in the waste received from the heat chamber.

19. An apparatus for treating waste, comprising a gravity drop steam heating tower for heating the waste to the biological kill temperature using pressurized steam, the gravity drop steam heating tower having an interior, an upper end portion, and a lower end portion, a first feed member for feeding the waste to be sterilized to the gravity drop steam heating tower, and a first vaporization system, the first vaporization system including (a) a heating chamber for facilitating vaporization of liquids in the waste, the heating chamber including a conveying member for conveying the waste from the lower end portion of the gravity drop steam heating tower into and through the heating chamber, and (b) a vaporization chamber for receiving the waste from the heating chamber and for releasing vapor entrained in the waste into the vaporization chamber, the apparatus further including at least one additional vaporization system, each additional vaporization system positioned in the apparatus serially after the vaporization system preceding it, with the conveying member of each additional vaporization system conveying waste from the vaporization chamber of the vaporization system immediately preceding it.

20. The apparatus of claim 19, each vaporization chamber having vaporization vent and vaporization vent fan in communication therewith for producing a negative pressure in the vaporization chamber to promote flash off of moisture and removal of vapors from the vaporization chamber conveyed in the waste received from the heat chamber.

21. The apparatus of claim 19, the conveying member of the first vaporization system being a screw conveyor that creates a seal between the gravity drop steam heating tower and the vaporization chamber of the first vaporization system, and each conveying member of each additional vaporization system being a screw conveyor that creates a seal between the preceding vaporization chamber and its own vaporization chamber.

22. The apparatus of claim 19, the apparatus having an interior, each additional vaporization system having an entrance opening through which the waste material enters, each additional vaporization system having a surge area located outside its entrance opening, each surge area having a surge pressure monitor, and each monitor comprising a frame mounted in the surge area around an opening formed in the surge area, a flexible membrane mounted in the frame and over the opening in the surge area, the flexible membrane having a surface in contact with the interior of the apparatus, a hinged door mounted adjacent to the membrane outside the surge area, a plunger mounted on the door and extending into contact with the membrane for causing the membrane to bulge into the interior of the apparatus when the door is in a closed position, an extension spring extending between the frame and the door for biasing the door to be in a closed position, and a sensor positioned to detect when the door has been pushed open by the membrane due to surge pressure created in the surge area as the surge area approaches becoming overfull.

23. The apparatus of claim 22, further including a controller for controlling operation of the waste treatment apparatus, the controller being in communication with each sensor and responsive thereto.

24. The apparatus of claim 19, further including a controller, in communication with the conveying member of the heating chamber of the first vaporization system and in communication with the conveying member of each additional vaporization system, for controlling flow of waste material into and through each vaporization system.

25. An apparatus for treating waste, comprising a gravity drop steam heating tower for heating the waste to the biological kill temperature using pressurized steam, the gravity drop steam heating tower having an interior, an upper end portion, and a lower end portion, a first feed member for feeding the waste to be sterilized to the gravity drop steam heating tower, and a first vaporization system, the first vaporization system including (a) a heating chamber for facilitating vaporization of liquids in the waste, the heating chamber including a conveying member for conveying the waste from the lower end portion of the gravity drop steam heating tower into and through the heating chamber, and (b) a vaporization chamber for receiving the waste from the heating chamber and for releasing vapor entrained in the waste into the vaporization chamber, the vaporization chamber having an exit port through which the waste material that enters it is discharged, and further including a clamshell-type door for closing the exit port of the vaporization chamber to facilitate removal of vapor from the vaporization chamber through a vaporization chamber vent, the door having a counterbalance weight for biasing the door to a closed position, the door holding waste material introduced into the vaporization chamber until the waste material accumulated thereon outweighs the counterbalance weight, causing the door to open and the waste material accumulated thereon to discharge from the vaporization chamber.

26. An apparatus for treating waste, comprising a gravity drop steam heating tower for heating the waste to the biological kill temperature using pressurized steam, the gravity drop steam heating tower having an interior, an upper end portion, and a lower end portion, a first feed member for feeding the waste to be sterilized to the gravity drop steam heating tower, and a first vaporization system, the first vaporization system including (a) a heating chamber for facilitating vaporization of liquids in the waste, the heating chamber including a conveying member for conveying the waste from the lower end portion of the gravity drop steam heating tower into and through the heating chamber, and (b) a vaporization chamber for receiving the waste from the heating chamber and for releasing vapor entrained in the waste into the vaporization chamber, the apparatus further including a hopper from which the first feed member draws the waste to be sterilized, a material handling system positioned upstream of the hopper for feeding the waste to be sterilized to the hopper, and a de-misting and high efficiency particulate air filter system drawing off air from the hopper and the material handling system, the de-misting and high efficiency particulate air filter system including a de-misting filter for condensing any mist entrained in the air being drawn off, a high efficiency particulate air filter for collecting any airborne pathogens in the air being drawn off, and a fan for drawing off the air from the hopper and the material handling system and through the de-misting filter and the high efficiency particulate air filter to the atmosphere through a vent.

27. The apparatus of claim 26, the gravity drop steam heating tower having a sump at its lower end portion for discharging water from the gravity drop steam heating tower.

28. The apparatus of claim 27, further including a waste water evaporator, and drainage lines for transferring water from the de-misting filter and the sump to the waste water evaporator, the waste water evaporator having a chamber for holding water transferred therein through the drainage lines, and a heat exchanger positioned in the chamber for transferring heat into the water held in the chamber to heat the water to vaporization.

29. The apparatus of claim 28, further including a controller in communication with a steam feed line for controlling flow of steam to the heat exchanger.

30. An apparatus for treating waste, comprising a gravity drop steam heating tower for heating the waste to the biological kill temperature using pressurized steam, the gravity drop steam heating tower having an interior, an upper end portion, and a lower end portion, a first feed member for feeding the waste to be sterilized to the gravity drop steam heating tower, and a first vaporization system, the first vaporization system including (a) a heating chamber for facilitating vaporization of liquids in the waste, the heating chamber including a conveying member for conveying the waste from the lower end portion of the gravity drop steam heating tower into and through the heating chamber, and (b) a vaporization chamber for receiving the waste from the heating chamber and for releasing vapor entrained in the waste into the vaporization chamber, the interior of the gravity drop steam heating tower being defined by an interior wall, and further including a hot water spray down system mounted in the gravity drop steam heating tower for spraying the interior wall of the gravity drop steam heating tower with hot water to clean it, the hot water spray down system having a conduit mounted in the interior of the gravity drop steam heating tower, and a set of nozzles mounted along and in communication with the conduit, the nozzles being oriented to provide a spray of hot water to clean the interior wall of the gravity drop steam heating tower.

31. The apparatus of claim 30, further including a hot water supply line connecting the waste water evaporator to the conduit of the hot water spray down system for supplying hot water to the hot water spray down system from the waste water evaporator.

32. The apparatus of claim 30, further including a controller in communication with a hot water feed line for controlling flow of hot water to the hot water spray down system.

33. An apparatus for treating waste, comprising a gravity drop steam heating tower for heating the waste to the biological kill temperature using pressurized steam, the gravity drop steam heating tower having an interior, an upper end portion, and a lower end portion, a first feed member for feeding the waste to be sterilized to the gravity drop steam heating tower, and a first vaporization system, the first vaporization system including (a) a heating chamber for facilitating vaporization of liquids in the waste, the heating chamber including a conveying member for conveying the waste from the lower end portion of the gravity drop steam heating tower into and through the heating chamber, and (b) a vaporization chamber for receiving the waste from the heating chamber and for releasing vapor entrained in the waste into the vaporization chamber, the apparatus further including a surge pressure monitor mounted in a surge area located in the lower end portion of the gravity drop steam heating tower, the monitor comprising a frame mounted on the lower end portion of the gravity drop steam heating tower around an opening formed in the gravity drop steam heating tower, a flexible membrane mounted in the frame and over the opening in the gravity drop steam heating tower, the flexible membrane having a surface in contact with the interior of the gravity drop steam heating tower, a hinged door mounted adjacent to the membrane outside the gravity drop steam heating tower, a plunger mounted on the door and extending into contact with the membrane for causing the membrane to bulge into the interior of the gravity drop steam heating tower when the door is in a closed position, an extension spring extending between the frame and the door for biasing the door to be in a closed position, and a sensor positioned to detect when the door has been pushed open by the membrane due to surge pressure created in the surge area as the surge area approaches becoming overfull.

34. The apparatus of claim 33, further including
a controller for controlling operation of the waste treatment apparatus,
the controller being in communication with the sensor and responsive thereto.

35. An apparatus for treating waste, comprising
a gravity drop steam heating tower for heating the waste to the biological kill temperature using pressurized steam, the gravity drop steam heating tower having an interior, an upper end portion, and a lower end portion,
a first feed member for feeding the waste to be sterilized to the gravity drop steam heating tower, and
a first vaporization system, the first vaporization system including
(a) a heating chamber for facilitating vaporization of liquids in the waste, the heating chamber including a conveying member for conveying the waste from the lower end portion of the gravity drop steam heating tower into and through the heating chamber, and
(b) a vaporization chamber for receiving the waste from the heating chamber and for releasing vapor entrained in the waste into the vaporization chamber,
the apparatus further including
a controller for controlling operation of the waste treatment apparatus,
the controller being in communication with the first flow member for controlling flow of waste material into the gravity drop steam heating tower.

* * * * *